(12) United States Patent
Klein et al.

(10) Patent No.: US 6,737,051 B1
(45) Date of Patent: May 18, 2004

(54) CELL COMPOSITIONS CONTAINING MACROPHAGES, PRESENTING ANTI-INFECTIOUS AND HEMATOPOIETIC PROPERTIES

(75) Inventors: Bernard Klein, Saint-Clement-de-Riviere (FR); Zhao Yang Lu, Castelnau-le-Lez (FR); Jacques Bartholeyns, Turquant (FR)

(73) Assignees: I.D.M. Immuno-Designed Molecules, Paris (FR); Centre Hospitalier Universitaire de Montpellier, Montpellier Cedex (FR)

( * ) Notice: Subject to any disclaimer, the term of this patent is extended or adjusted under 35 U.S.C. 154(b) by 0 days.

(21) Appl. No.: 09/890,652

(22) PCT Filed: Jan. 27, 2000

(86) PCT No.: PCT/EP00/00647
§ 371 (c)(1),
(2), (4) Date: Nov. 27, 2001

(87) PCT Pub. No.: WO00/45827
PCT Pub. Date: Aug. 10, 2000

(30) Foreign Application Priority Data

Feb. 3, 1999 (EP) ............................................ 99400239

(51) Int. Cl.$^7$ .......................... A01N 63/00; C12N 5/00; C12N 5/08; C12N 5/02
(52) U.S. Cl. ...................... 424/93.1; 424/93.7; 435/325; 435/366; 435/373; 435/372; 435/391; 435/405
(58) Field of Search .............................. 424/93.7, 93.1; 435/366, 373

(56) References Cited

U.S. PATENT DOCUMENTS 5,672,346 A 9/1997 Srour et al.

FOREIGN PATENT DOCUMENTS

| EP | 0 241 578 | 10/1987 |
| EP | 0 451 611 | 10/1991 |
| WO | WO 92/21402 | 12/1992 |
| WO | WO 97/16535 | 5/1997 |

*Primary Examiner*—Christina Chan
*Assistant Examiner*—Michail A Belyavskyi
(74) *Attorney, Agent, or Firm*—Young & Thompson

(57) ABSTRACT

The invention relates to a cell composition containing macrophages, presenting anti-infectious and hematopoietic properties. More particularly, the invention relates to a cell composition containing macrophages, myeloid cells and progenitors; said cell compositions are useful for the restoration of hematopoiesis in an aplasic patient and/or the protection of patients against infectious diseases or against residual tumors.

16 Claims, 3 Drawing Sheets

Figure 3:
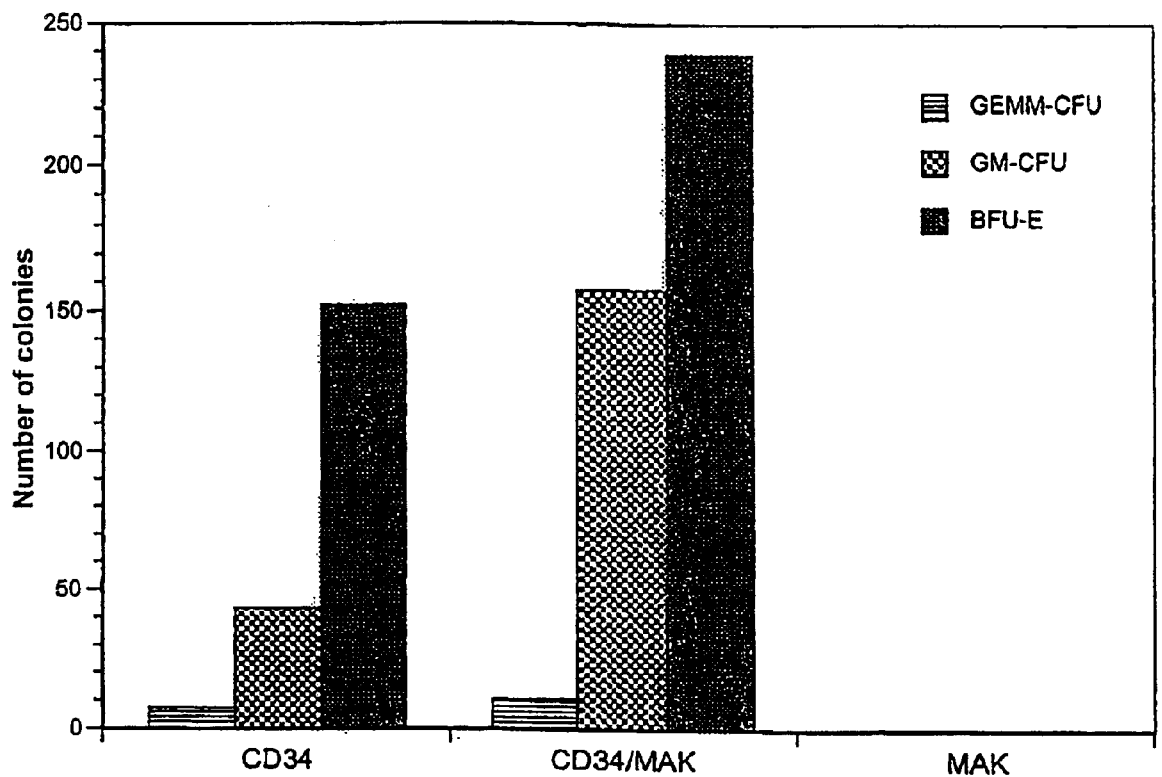

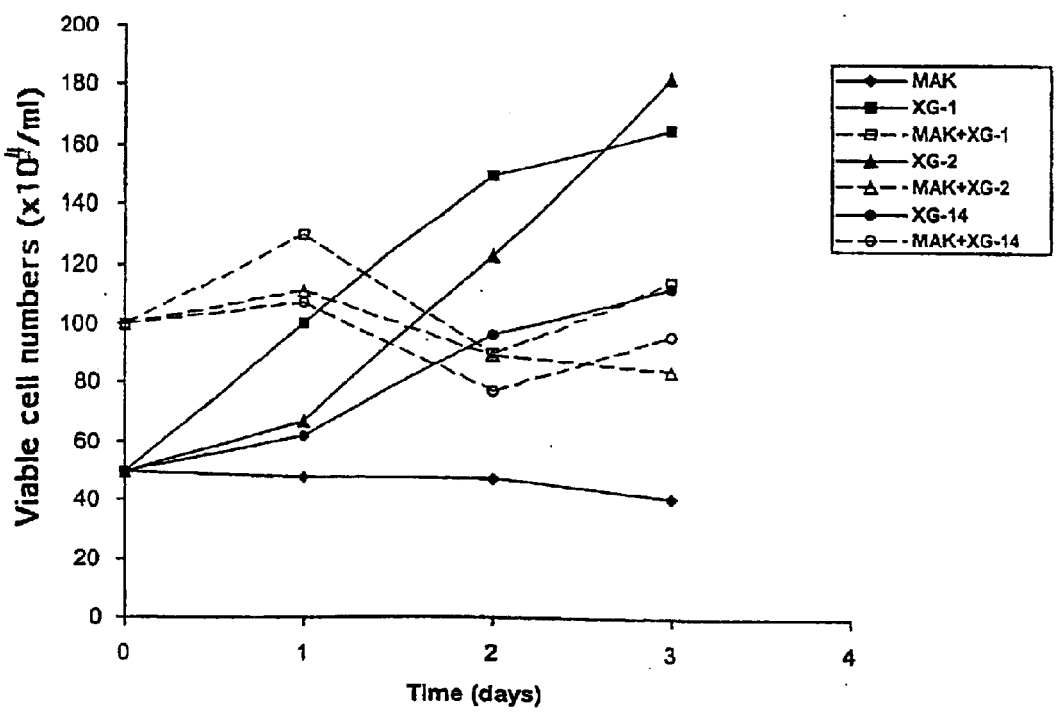
Figure 1. Myeloma cell lines cultured with or without MAK
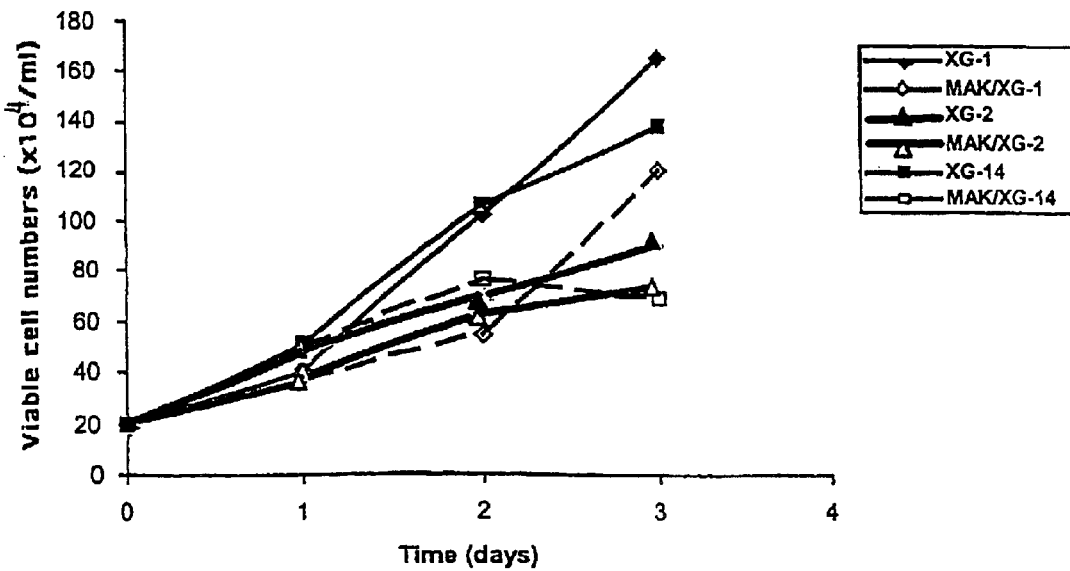
Figure 2. Myeloma cell lines cocultured with MAK through transwell culture plates

CELL COMPOSITIONS CONTAINING MACROPHAGES, PRESENTING ANTI-INFECTIOUS AND HEMATOPOIETIC PROPERTIES The invention relates to a cell composition containing macrophages, presenting anti-infectious and hematopoietic properties, and a process for preparing the same.

Peripheral hematopoietic apheresis instead of bone marrow puncture and purification are widely used to collect hematopoietic progenitor cells. These cells are used in allogeneic or autologous transplantations for the treatment of genetic diseases and mainly of neoplasic diseases to support high dose chemotherapy or radiotherapy.

Positive selection of the apheresis products for cells bearing the CD34 antigen ($CD34^+$ stem cells) and cryopreservation until use has become a recognized method.

However, it offers several drawbacks including cost (the process of selection of cells on antibody coated beads), limited amounts of progenitor cells recovered, and delays in immune reconstitution (resulting in infectious complications in the post transplant period).

The number of progenitor cells present in blood can be increased by the preapheresis conditioning of the patient treated with GM-CSF and/or G-CSF colony stimulating factors and eventually with chemotherapy drug such as a cyclophosphamide.

However, cancer patients often relapse due to the presence of residual tumor cells resistant to the chemotherapy regimen (Bhatia M et al.: Quantitative analysis reveals expansion of human hematopoietic repopulating cells after short-term ex vivo culture. *J Exp Med.* 186: 619–624, 1997, Bonnet D et al.: Cytokine treatment or accessory cells are required to initiate engrafment of purified primitive human hematopoietic cells transplanted at limiting doses into NOD/SCID mice, *Bone Marrow Transplant.* 23: 203–209, 1999, Breems D A et al.: Stroma-contact prevents loss of hematopoietic stem cell quality during ex vivo expansion of CD34+ mobilized peripheral blood stem cells. *Blood.* 91: 111–117, 1998, Civin et al.: Highhly purified CD34-positive cells reconstitute hematopoiesis. *J Clin Oncol.* 14: 2224–2233, 1996, Morrison S J et al.: The biology of hematopoietic stem cells. *Annu Rec Cell Dev Biol.* 11: 35–71, 1995, Traycoff C M et al.: Proliferation-induced decline of primitive hematopoietic progenitor cell activity is coupled with an increased in apoptosis of ex vivo expanded CD34+ cells. *Exp Hematol.* 26: 53–62, 1998).

An aim of the invention is to provide a new cell composition containing macrophages, presenting interesting properties in cancer immunotherapy and in stem cell transplantation.

Another aim of the present invention is to provide a new cell processing method allowing under improved standardised procedures the expansion of progenitor and stem cells from peripheral blood without costly purification of a defined cell population.

The aims of the invention are achieved by a cell composition containing macrophages, myeloid cells and progenitor cells, with said progenitor cells being preferably present in a mean ratio of at least about 1%, preferably about 0.1 to 20%, with said myeloid cells being preferably present in an amount of about 10% to about 30%, with said macrophages being preferably in an amount of about 10 to about 70%, these percentages being expressed with respect to the total number of cells.

Macrophages, myeloid cells and progenitor cells are defined as $CD14^+$ and $CD64^+$ cells (macrophages), $CD33^+$ cells (myeloid cells) and $CD34^+$ cells and/or GM-CFU (progenitor cells). GM-CFU are cells able to form colonies of granulocyte and macrophage in cytokine containing semi-solid culture medium after 14 days of culture.

GEMM-CFU are myeloid stem cells, and are able to give BFU-E, CFU-GM, CFU-M, CFU-EO, and CFU-B. BFU-E are progenitor cells able to differentiate into erythrocytes.

According to an advantageous embodiment, the cell composition of the invention contains T lymphocytes, preferably in a ratio of about 10 to 60%, expressed with respect to the total number of cells.

According to an advantageous embodiment of the invention, the progenitor cells contain from about 0.1 to about 20% of stem cells, expressed with respect to the total number of progenitor cells.

Stem cells are defined as expressing CD34 molecules and/or by their ability to form colonies in cytokine containing semi-solid culture medium.

According to an advantageous embodiment, the progenitor cells are generated from and possibly included in peripheral blood mononuclear cells, and in particular are chosen among:

myelo-erythroid progenitor cells, myeloid progenitor cells, lymphoid progenitor cells or a mixture thereof.

The expression "included in" means that the progenitor cells are present in the cell composition.

The expression "generated from" means that the progenitor cells are differentiated from stem cells originally present in the cell composition.

In the cell composition of the invention, the macrophages, myeloid cells and the lymphocytes if present, are included in/or generated from blood mononuclear cells.

The cell composition of the invention has gained a new combination of activities useful in cancer immunotherapy and in stem cell transplantation. These properties include:

1) purge by macrophages and cytotoxic T/NK cells of the tumor cells eventually present in the graft,
2) eradication of residual cancer disease in the patient by macrophages and/or antigen presenting cells (MAC-DCs dendritic cells) present in the autologous or in the allogeneic graft,
3) avoiding most infectious episodes after injection at the beginning of the aplasia period following therapy in the patient, thanks to the potent anti-viral, anti-bacterial and anti-parasite properties of macrophages and eventually of contaminating polynuclear cells and their precursors present in the product,
4) facilitating engraftment by the enhanced amount of stem cells, of hematopoietic cells, progenitors of myeloid cells, erythroid and lymphoid as well as of cells at intermediate states of differentiation present in the graft,
5) decrease significantly of the aplasia period (correlated with patient's fever and infections) by markedly increasing the recovery rate of the different blood populations.

The invention also relates to a process for the preparation of a cell composition containing macrophages, myeloid cells and progenitor cells, with said progenitor cells being preferably present in an amount of about 0.1% to about 10%, with said macrophages being preferably in an amount of about 10 to about 60%, these percentages being expressed with respect to the total number of cells, comprising the step of mobilization of the progenitor cells in the blood of a patient, for instance by premeditation of said patient with G-CSF and/or GM-CSF, or G-CSF and cyclophophosphamide, thus increasing the amount of progenitor cells in peripheral blood.

The term "mobilization" means stimulation of bone marrow cells to release increased amount of progenitor cells in the blood.

The process of the invention can comprise an additional step of coculture of the blood mononuclear cells and progenitors, after washing off the platelets, the granulocytes and erythrocytes, for about 4 to about 10 days, in a medium allowing differentiation of monocytes into macrophages and myeloid progenitors into polynuclear cells.

According to an advantageous embodiment of the process, the coculture of the blood mononuclear cells and progenitors is carried out in the presence of cytokines or growth factors, for example: IL3, IL6, stem cell factor, EPO, thrombopoietin, GM-CSF, G-CSF, Flat-3 ligand, c-kit ligand or their agonists.

The process of the invention can also comprise an additional step of macrophage activation, at the end of the coculture, for instance by addition of γ-interferon or muramyl peptides.

The aim of activation macrophages is to gain more anti-infectious and anti-tumoral activity.

The process of the invention can comprise an additional step of concentration of the cells obtained at the end of the coculture, and resuspension in a vehicle suitable for administration to a patient.

The process of the invention can comprise after the resuspension of the coculture, a step of freezing part or the totality of the resuspension.

It is to be noted that cellular product obtained after ex vivo differentiation and expansion contains stem cells, progenitor cells, myeloid cells, T lymphocytes and differentiated macrophages which are activated (for example by γ interferon) at the end of the process. The coculture for 3 to 12 days performed at 37° C. in non adherent bags and defined medium (IMDM basis) allows increased recovery of $CD34^+$ cells and/or of intermediate hematopoietic progenitor cells. This means that normal hematopoietic progenitors are not only spared by activated macrophages, but are also stimulated to greater proliferation and differentiation.

The invention also relates to a cell composition such as obtained according to the process as defined above.

The invention also relates to a pharmaceutical composition containing, as active substance, a cellular composition as defined above.

The invention also relates to a method for the restoration of hematopoiesis in an aplasic patient and/or the protection of patients against infectious diseases or against residual tumors, comprising the use of a pharmaceutical composition as defined above.

The expression "restoration of hematopoiesis" means increasing the level of hematopoietic cells to reach a normal functionality similar to that of healthy individuals to achieve protection against infections (which can be measured by blood numeration and identification).

The invention also relates to a method for the diminution of the aplasia period in a patient, for instance from 11 days to 1 to 3 days, comprising the use of pharmaceutical composition as defined above.

The term "aplasia" is defined as a pathological low level of hematopoietic cells in blood.

The cell composition of the invention defined above is characterised by the fact that it is derived from and/or included in a peripheral blood mononuclear cell composition containing:

from about 10 to about 50% of monocytes, from about 10 to about 70% of lymphocytes, from about 0,1 to about 20% of progenitor cells, from about 1 to about 50% of polynuclear cells, from about 0,1 to about 20% of stem cells.

Figure Legend

FIG. 1 represents the inhibition of the growth of myeloma cell lines of the activated MAK.

The number of viable cells ($\times 10^4$/ml) is plotted against the time (expressed in days).

The XG-1, XG-2, XG-14 myeloma cell lines were cultured in RPMI1640 with 10% FCS and 3 ng/ml of IL-6 at a concentration of $5\times10^5$ cells/ml. The characteristics of the XG-1 and XG-2 cell lines are described in Blood 83: 3654–3663, 1994 and those of XG-14 in Journal of Immunology, 163: 514–524, 1999. Cells were cultured in teflon coated culture wells. Myeloma cells were cultured either alone or with $5\times10^5$ activated MAK. In one group, only MAK were cultured. Every day, the number of viable cells was determined using trypan blue exclusion. The percentage of myeloma cells was determined by staining with anti-CD38 antibodies and FACS analysis. Results are those of one representative experiment out of three.

The curve with lozenges corresponds to MAK.

The curve with black squares corresponds to XG-1

The curve with hollow squares corresponds to MAK+ XG-1.

The curve with black triangles corresponds to XG-2.

The curve with hollow triangles corresponds to MAK+ XG-2.

The curve with black circles corresponds to XG-14.

The curve with hollow Circles Corresponds to MAK+ XG-14.

FIG. 2 represents the inhibition of myeloma cell growth by activated macrophages producing soluble mediators.

The number of viable cells ($\times 10^4$/ml) is plotted against the time (expressed in days).

XG-1, XG-2 and XG-14 myeloma cells were cultured in RPMI 1640, 10% FCS and 3 ng/ml of IL-6. $2\times10^5$ myeloma cells were cultured in the lower chamber of transwell culture wells containing or not containing $2\times10^5$ MAK in the upper chamber. Every day, the number of viable myeloma cells was determined using trypan blue exclusion. Results are those of one representative experiment out of two.

The curve with black lozenges corresponds to XG-1.

The curve with hollow lozenges corresponds to MAK/XG-1.

The curve with black triangles corresponds to XG-2.

The curve with hollow triangles corresponds to XG-2.

The curve with black squares corresponds to XG-14.

The curve with hollow squares corresponds to MAK XG-14.

FIG. 3 represents the stimulation of the generation of hematopoietic colonies by activated MAK.

$2\times10^3$ purified CD34 cells (purity>90%) were cultured in methyl cellulose semi-solid culture medium and hematopoietic cytokines either alone or with $10^5$ activated MAK. The number of GM-CFU, BFU-E and GEMM-CFU was enumerated after 14 days of culture. Results are those of one representative experiment out of three.

The Y axis represents the number of colonies.

In the X axis, the columns with parallel lines represent GEMM-CFU, the columns with black and white squares represent GM-CFU and the grey columns represent BFU-E.

Figure 4:
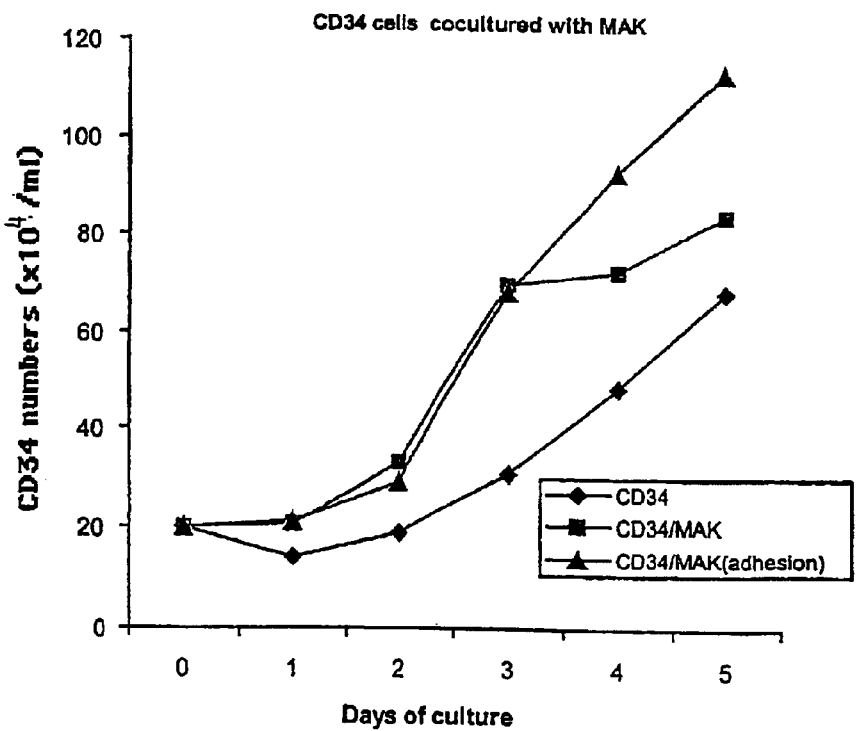

FIG. 4 represents the stimulation of the growth of CD34 cells by activated MAK.

Purified CD34 cells (purity>90%) were cultured in RPMI1640, 10% FCS and 50 ng/ml of IL-3 and SCF. The number of CD34 cells was determined every day using labelling with anti-CD34 antibody and FACS analysis. CD34 cells were culture either alone or with $10^5$ activated MAK. Results are those of one representative experiment out of two.

The Y axis represents the CD 34 numbers ($\times 10^4$/ml) and the X axis represents the time (expressed in days of culture).

The curve with lozenges corresponds to CD34.

The curve with squares corresponds to CD34/MAK.

The curve with triangles corresponds to CD34/MAK (adhesion).

Figure 5:
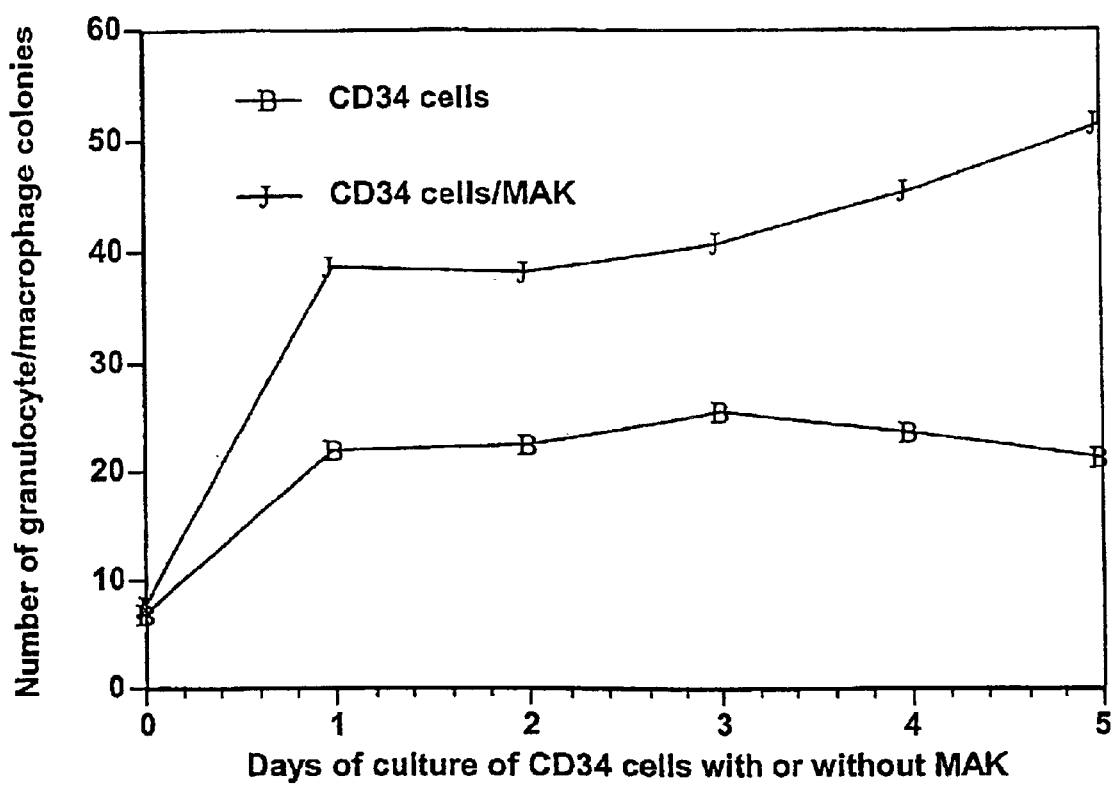

FIG. 5 represents the stimulation of the growth of hematopoietic progenitors by activated MAK.

Purified CD34 cells were cultured as described in FIG. 4. Every day, the number of hematopoietic progenitors was evaluated by culture in methyl cellulose semi-solid culture medium and hematopoietic cytokines. The number of GM-CFU was enumerated after 14 days of culture.

The Y axis represents the number of granulocytes/macrophages colonies.

The X axis represents the days of culture of CD34 cells with or without MAK.

The curve with "B" corresponds to CD34 cells and the curve with "J" corresponds to CD34 cells/MAK.

In the examples hereafter, the abbreviations used have the following meanings:

CD: Cluster of Differentiation, DMSO: Dimethylsulfoxyde, RPMI: Rosewell Park Medical Institute, FCS: Fetal Calf Serum, FACS: Fluorescence Activated Cell Sorting, SCF: Stem Cell Factor.

EXAMPLE 1

A patient with multiple myeloma was treated with cyclophosphamide (4 g/m$^2$) and a daily injection of G-CSF (5 µg/kg). The peripheral blood CD34 count was monitored every day and apheresis was started when CD34 count was greater than 10/mm$^3$. Mononuclear cells (less than 10% polynuclear cells) were collected by apheresis, washed twice in PBS, and cultured for 6 days in a MAK TM cell processor at a concentration of $5 \times 10^6$ cells/ml in 2 culture bags of 500 ml, at 37° C., 5% CO$_2$. The culture medium contained 500 U/ml of GM-CSF. On day 6, IFN-gamma (250 U/ml) was added for one day. Before culture, and at day 1, 2, 5, 6, 7 of culture and after elutriation, a cell sample was harvested for determination of the cell count and of the percentages of CD34, CD14, CD33, CD64, HLA-DR, CD16, CD3 cells and of the concentration of granulocyte-macrophage colony forming units (GM-CFU). The cell membrane phenotype of the cells was determined by FACS analysis using FITC labeled murine monoclonal antibodies (Imnunotech, Marseilles, France) or isotype control murine antibodies. The concentration of GM-CFU was determined using methylcellulose semi solid medium containing various hematopoietic cytokines purchased from Stemgen (Villejuif, France).

Progressive 3-fold increase of the numbers of CD34 cells and of GM-CFU has been observed. These data indicated that this culture system supported the growth of hematopoietic precursors.

Cells from apheresis (mobilized myeloma patients) could also be kept frozen. After thawing $5.7 \times 10^9$ cells containing 44% CD3$^+$ cells (lymphocytes) and 42% CD14$^+$ cells (monocytes) could be seeded and cultured in defined medium at 37° C.

Lymphocytes (CD3$^+$) and CD14$^+$ cells tended to decrease (see table 1). CD64$^+$ macrophages were low until activation by IFNγ at day 6, which increased markedly this population. This last population was mainly present after purification by elutriation at day 7.

When the subpopulation of CD34$^+$ stem cells was followed along the culture, it was observed an increase in the number and percentage of cells with CD34$^+$ phenotype. $7.10^7$ CD34$^+$ cells were present at the beginning of culture, increasing to $21.10^7$ after 6 days (Table 1).

The presence of cytokines released in the culture medium and of a large number of T lymphocytes (57% in this experiment) appeared important for the proliferation of CD34$^+$ and progenitor cells. Macrophages were obtained reproducibly, with good viability after thawing. They could eventually be purified to 90% by elutriation with and average of $5.10^9$ macrophages differentiated from one apheresis (60 patients analyzed). The total cell population recovered after culture is injected to patients to allow faster recovery of hematopoietic progenitors and decrease the period of aplasia.

TABLE 1

| Culture | J1 | J2 | J5 | J6 | Before Elutriation | After Elutriation |
|---|---|---|---|---|---|---|
| Volume (ml) | 1000 | 1000 | 1000 | 1000 | 1000 | 1000 | 228 |
| Cellular concentration ($10^6$/ml) | 5 | 3.3 | 2.6 | 1.8 | 1.6 | 1.5 | 1.5 |
| Total number of cells ($10^9$) | 5 | 3.3 | 2.6 | 1.8 | 1.6 | 1.5 | 0.34 |
| CD 3 (%) | 57 | 33 | 27 | 15 | 23 | 19 | 1.3 |
| CD 14 (%) | 41 | 9.25 | 18 | 8.5 | 8 | 13 | 40. |
| CD 16 (%) | 34 | 11.25 | 4 | .62 | 1 | 2 | 3.9 |
| CD 64 (%) | 28 | nd | 0.2 | 4.28 | 0.79 | 15 | 59 |
| HLA-Dr (%) | 60 | nd | 19 | 33.4 | 64 | 37 | 73 |
| CD 33 (%) | nd | nd | nd | 14 | 27 | 43 | 47 |
| CD 34 (%) | 1.41 | nd | 7.29 | 11 | 13 | 14 | 21 |
| CFU-GM (/$10^5$) | 116 | nd | nd | nd | 1000 | nd | 14 |
| BFU (/$10^5$) | 197 | nd | nd | nd | 2680 | nd | nd |

EXAMPLE 2

Objectives

In the figures and in the following example, activated macrophages (MAK) are obtained according to PCT/EP93/01232.

Activated macrophages (MAK) are able to kill various human tumor cells. We have looked for whether MAK generated from apheresis cells—collected during hematopoietic stem cell mobilisation in the peripheral blood by cyclophosphamide and granulocyteolony stimulating factor (G-CSF)—are able to kill human malignant plasma cells. We have also looked for their effect on the growth of human hematopoietic CD34 stem cells and on the ability of CD34 cells to generate hematopoietic colonies in semi solid culture medium.

Generation of MAK

Activated MAK were obtained using kits provided by IDM (Paris, France). MAK were generated from apheresis cells from 2 patients collected during mobilization of hematopoietic stem cells in the peripheral blood using cyclophosplaride and GCSF. Apheresis cells were cultured for 6 days with 500 ng/ml of GM-CSF and then for an additional day with IFN-gamma (250 U/ml). At day 7, MAK were purified by counter elutriation. We have previously shown that these cells comprised more than 80–90% of MAK expressing HLA-DR and CD64 molecules (Patent deposit No. 99 400 239.2). MAK were frozen with a physiologic NaCl solution, 4% albumin and 10% DMSO. For the manipulations described below, MAK were thawed and cultured for one day with RPMI1640, 10% FCS (Biowittaker, Belgium) and 500 U/ml GM-CSP before use.

Effect of MAK on the Growth of Malignant Plasma Cell Lines

Three malignant plasma cell lines have been obtained in the laboratory: XG-1, XG-2, XG-14. The survival and the growth of these cell lines are dependent on the addition of exogenous cytokines. Cultures were done in 24 well culture plated coated with teflon (Polylabo Block, ref. 80776) in order to avoid adherence of MAK. Cells were cultured in RPMI1640 culture medium supplemented with 10% FCS (Biowittaker, Belgium) and 3 ng/ml of interleuli6 (Sandoz, Switzerland). $5 \times 10^5$ myeloma cells were cultured alone or with $5 \times 10^5$ activated MAK for 3 days. In one culture group, $5 \times 10^5$ MAK were cultured alone. At day 1, 2 and 3 of cultures, the number of viable cells was determined using trypan blue exclusion. As shown in FIG. 1, addition of MAK blocked the growth of the 3 myeloma cell lines. We looked for whether MAK phagocytised myeloma cells or secreted a soluble factor able to block myeloma cell growth. Cocultures were performed using transwell culture wells with two chambers separated by a 0.45 μm filter. $2 \times 10^5$ activated MAK were cultured in 100 μl of culture medium in the upper chamber and in the lower chamber, $2 \times 10^5$ cells myeloma cells were plated in 600 μl culture medium containing 3 ng/ml of IL-6. Myeloma cell numbers were determined on day 1, 2 and 3 of culture. As shown in FIG. 2, addition of activated MAK reduced myeloma cell growth. This reduction was inferior to that found when activated MAK were in contact to myeloma cells. These data indicated that activated MAK inhibited myeloma cell growth partly by producing a soluble inhibitory factor.

Effect of Activated MAK on the Growth and Differentiation of Hematopoietic CD34 Stem Cells The effects of activated MAK on the growth of CD34 cells and on their ability to differentiate into hematopoietic cells were investigated. First, activated MAK were cocultured with purified human CD34 cells (>90% CD34 cells) in methyl cellulose semi-solid culture medium containing a cocktail of hematopoietic cytokines for 14 days (Stemgem, France). On day 14, the number of granulocyte-macrophage colonies (GM-CFU), burst forming unit erythroid (BFU-E) and mixed colonies (GEMM-CFU) was determined. As outlined in FIG. 3, addition of activated MAK increased the number of hematopoietic colonies indicating that activated MAK did not affect CD34 cells but on the contrary amplified their differentiation into hematopoietic colonies. In another experiment, activated MAK were cocultured with purified CD34 cells for several days in the presence of interleukin-3 (IL-3) and stem cell factor (SCF). Every day, the number of CD34 cells was determined by staining with an anti-CD34 monoclonal antibody and FACS analysis. The number of hematopoietic progenitor was determined by culture in methyl cellulose semi solid culture medium containing hematopoietic cytokines. As shown in FIG. 4 and 5, activated MAK increased the growth of CD34 cells as well as of hematopoietic progenitors.

In conclusion, activated MAK have no inhibitory effect on the growth and differentiation of hematopoietic CD34 cells. On the contrary, activated MAK stimulate the short-term growth of CD34 stem cells and of hematopoietic progenitors.

What is claimed is:

1. A cell composition, comprising:

macrophages present in an amount of about 10 to about 70%, said percentage is expressed with respect to the total number of cells;

and progenitor cells present in an amount of at least 0.1%, said percentage being expressed with respect to the total number of cells.

2. The cell composition according to claim 1, wherein said progenitor cells are present in an amount of about 0.1 to about 20%, said percentage being expressed with respect to the total number of cells.

3. The cell composition according to claim 1, further comprising myeloid cells, said myeloid cells are present in an amount of about 10% to about 30%, said percentage being expressed with respect to the total number of cells.

4. The cell composition according to claim 1, wherein said progenitor cells contain from about 0.1 to about 20% of stem cells, expressed with respect to the total number of progenitor cells.

5. A composition comprising, a pharmaceutically acceptable carrier and as an active substance, the cell composition according to claim 1.

6. The cell composition according to claim 1, wherein said composition is derived from a peripheral blood mononuclear cell composition containing:

from about 10 to about 50% of monocytes, from about 10 to about 70% of lymphocytes, from about 0.1 to about 20% of progenitor cells, from about 1 to about 50% of polynuclear cells, and from about 0.1 to about 20% of stem cells.

7. A cell composition comprising macrophages, myeloid cells and progenitor cells, said progenitor cells are present in an amount of about 0.1% to about 20%, said macrophages are in an amount of about 10 to about 70%, and said percentages are expressed with respect to the total number of cells, as obtained by a process comprising the following steps:

collecting mononuclear cells and progenitors by apheresis co-culturing blood mononuclear cells and progenitors, after washing of platelets, granulocytes and erythrocytes, for 4 to 10 days, in a medium allowing differentiation of monocytes into macrophages and myeloid progenitors into polynuclear cells.

8. A cell composition comprising macrophages, myeloid cells and progenitor cells, wherein said progenitor cells are present in an amount of about 0.1% to about 20%, said macrophages being in an amount of about 10 to about 70%, said percentages are expressed with respect to the total number of cells, as obtained by a process comprising the following steps:

mobilizing progenitor cells in the blood of a patient by premedication of said patient with G-CSF and/or GM-CSF or G-CSF and cyclophosphamide, collecting mononuclear cells and progenitors by apheresis, co-culturing of the blood mononuclear cells and progenitors, after washing of platelets, granulocytes and erythrocytes, for 4 to 10 days, in a medium allowing differentiation of monocytes into macrophages and myeloid progenitors into polynuclear cells.

9. A composition comprising, a pharmaceutically acceptable carrier and as an active substance, the cell composition according to claim 2.

10. A composition comprising, a pharmaceutically acceptable carrier and as an active substance, the cell composition according to claim 3.

11. A composition comprising, a pharmaceutically acceptable carrier and as an active substance, the cell composition according to claim 4.

12. The cell composition according to claim 2, wherein said composition is derived from a peripheral blood mononuclear cell composition containing:

from about 10 to about 50% of monocytes, from about 10 to about 70% of lymphocytes, from about 0.1 to about 20% of progenitor cells, from about 1 to about 50% of polynuclear cells, and from about 0.1 to about 20% of stem cells.

13. The cell composition according to claim 3, wherein said composition is derived from a peripheral blood mononuclear cell composition containing:

from about 10 to about 50% of monocytes, from about 10 to about 70% of lymphocytes, from about 0.1 to about 20% of progenitor cells, from about 1 to about 50% of polynuclear cells, and from about 0.1 to about 20% of stem cells.

14. The cell composition according to claim 4, wherein said composition is derived from a peripheral blood mononuclear cell composition containing:

from about 10 to about 50% of monocytes, from about 10 to about 70% of lymphocytes, from about 0.1 to about 20% of progenitor cells, from about 1 to about 50% of polynuclear cells, and from about 0.1 to about 20% of stem cells.

15. The cell composition according to claim 7, wherein said medium contains at least one component selected from the group consisting of cytokines and growth factors.

16. The cell composition according to claim 8, wherein said medium contains at least one component selected from the group consisting of cytokines and growth factors.

* * * * *